United States Patent [19]

Dupuis

[11] Patent Number: 5,679,328
[45] Date of Patent: Oct. 21, 1997

[54] THICKENING COMBINATION BASED ON GUAR GUM OR ON NONIONIC CELLULOSE GUM AND ON A CROSSLINKED POLYMER AND COSMETIC OR DERMATOLOGICAL HAIR OR SKIN TREATMENT COMPOSITION CONTAINING SUCH A COMBINATION

[75] Inventor: Christine Dupuis, Paris, France

[73] Assignee: L'Oreal, Paris, France

[21] Appl. No.: 507,318

[22] PCT Filed: Feb. 16, 1994

[86] PCT No.: PCT/FR94/00170

§ 371 Date: Aug. 22, 1995

§ 102(e) Date: Aug. 22, 1995

[87] PCT Pub. No.: WO94/18935

PCT Pub. Date: Sep. 1, 1994

[30] Foreign Application Priority Data

Feb. 23, 1993 [FR] France ............... 93 02065

[51] Int. Cl.$^6$ ............... A61K 7/11; A61K 7/15; A61K 7/42; A61K 47/36
[52] U.S. Cl. ............... 424/70.13; 424/70.17; 424/59; 424/DIG. 2; 514/880; 514/881
[58] Field of Search ............... 424/401, 489, 424/487, 70.13, 70.17, 70.24, 70.27, 70.28, 59–60, 450, DIG. 2, DIG. 4; 514/852, 859, 864, 880, 881, 937, 942; 252/315.3, DIG. 13, DIG. 5

[56] References Cited

U.S. PATENT DOCUMENTS

| | | | |
|---|---|---|---|
| 4,425,241 | 1/1984 | Swanson | 507/120 |
| 5,089,252 | 2/1992 | Grollier et al. | 424/70.16 |
| 5,525,356 | 6/1996 | Jevne et al. | 424/486 |

FOREIGN PATENT DOCUMENTS

| | | |
|---|---|---|
| 0 200 620 | 11/1986 | European Pat. Off. . |
| 0 524 434 | 1/1993 | European Pat. Off. . |
| 0 152 095 | 8/1995 | European Pat. Off. . |
| WO 92/21316 | 12/1992 | WIPO . |

*Primary Examiner*—Edward J. Webman
*Attorney, Agent, or Firm*—Jacobson, Price, Holman & Stern, PLLC

[57] ABSTRACT

A thickening mixture containing, in an aqueous medium, (a) a component (A) consisting of at least one guar gum or non-ionic cellulose having no hydrophobic group, with a viscosity in solution of over 15 cps at 15 wt % in water, as measured by DRAGE module 2 at 25° C.; (b) a component (B) consisting of at least one cross-linked polymer selected from (i) acrylamide and ammonium acrylate copolymers; (ii) acrylamide and partially or totally neutralized 2-acrylamido 2-methylpropane sulphonic acid copolymers; (iii) acrylamide and methacryloyl oxyethyl trimethylammonium chloride copolymers; and (iv) methacryloyl oxyethyl trimethylammonium chloride homopolymers; wherein the weight ratio of crosslinked polymer active material to guar gum or cellulose is 0.2–10. A cosmetic or dermatological hair- or skin-care composition containing said mixture is also provided.

19 Claims, No Drawings

THICKENING COMBINATION BASED ON GUAR GUM OR ON NONIONIC CELLULOSE GUM AND ON A CROSSLINKED POLYMER AND COSMETIC OR DERMATOLOGICAL HAIR OR SKIN TREATMENT COMPOSITION CONTAINING SUCH A COMBINATION

This application is a 371 of PCT/FR94/00170 filed Feb. 16, 1994.

The invention relates to a thickening combination based on guar gums or on nonionic cellulose gums having no hydrophobic group and on specific crosslinked polymers and to a cosmetic or dermatological hair or skin treatment composition containing such a combination.

In order to contribute softness to hair or to the skin or alternatively to facilitate disentangling of hair, certain crosslinked polymers such as crosslinked acrylamide copolymers or polymers are used in cosmetics or in dermatology. These polymers have viscosities which make it possible to obtain appropriate thickening properties for cosmetic and dermatological formulations, good softness properties for hair or the skin and a pleasant feel.

However, the viscosity of these crosslinked polymers is very sensitive to additives such as alcohols, certain anionic or cationic polymers or certain antidandruff agents. The addition of these additives can cause fluidification phenomena which are undesirable for the texture of cosmetic or dermatological formulations containing these crosslinked polymers.

The Applicant Company has surprisingly discovered that, by combining specific thickeners chosen from guar gums and nonionic cellulose gums having no hydrophobic group with certain crosslinked polymers, a viscosity synergetic effect was observed for the crosslinked polymers which makes it possible to overcome the disadvantages mentioned above.

The specific combination in accordance with the present invention makes it possible to prepare cosmetic or dermatological compositions based on crosslinked polymers in the gel, cream, emulsion or dispersion form whose rheological properties are substantially improved.

One subject of the invention is therefore composed of a thickening combination based on guar gum or on nonionic cellulose gum having no hydrophobic group and on specific crosslinked polymers.

A subject of the invention also relates to a cosmetic or dermatological composition containing such a combination.

Another subject relates to cosmetic hair or skin treatment processes using these compositions according to the desired application.

Other subjects will become apparent in the light of the following description and examples.

The present invention mainly relates to a thickening combination, which comprises, in an aqueous medium:
 a) a component (A) comprising at least one guar gum or nonionic cellulose gum, having no hydrophobic group, having a viscosity, as a 1.5 weight % solution in water, measured with a Drage unit 2 at 25° C., greater than 15 cps;
 b) a component (B) comprising at least one crosslinked polymer chosen from:
  (i) acrylamide and ammonium acrylate copolymers;
  (ii) acrylamide and partially or totally neutralized 2-acrylamido-2-methylpropanesulfonic-acid [sic] copolymers;
  (iii) acrylamide and methacryloyloxyethyltrimethylammonium chloride copolymers;
  (iv) methacryloyloxyethyltrimethylammonium chloride homopolymers.

The crosslinked polymer/guar gum or nonionic cellulose gum ratio, as weight of active material, is between 0.2 and 10 and preferably between 1 and 5.

Mention may be made, among the guar gums used according to the present invention, of:
 the hydroxypropylated guar gum sold under the name "Jaguar HP8" by the Company Meyhall;
 the guar gum sold under the name "Guargel D/15" by Société francaise des Colloïdes.

Mention may be made, among the nonionic cellulose gums used in accordance with the present invention, of:
 the methylhydroxypropylcellulose sold under the name "Methocel $F_4M$ Standard" by the Company Dow Chemical;
 the methylcellulose sold under the name "Methyl Cellulose 200" by the Company Laserson Sabetay;
 the hydroxyethylcellulose sold under the name "Natrosol HHR" by the Company Aqualon;
 the hydroxypropylcellulose sold under the name "Klucel H" by the Company Aqualon;
 the methylhydroxyethylcellulose sold under the name "Tylose MH300" by the Company Hoechst.

The crosslinked acrylamide-ammoniumacrylate copolymer used in accordance with the present invention is more particularly an acrylamide-ammonium acrylate (5/95 by weight) copolymer crosslinked by a crosslinking agent possessing olefinic polyunsaturation, such as divinylbenzene, tetraallyloxyethane, methylenebisacrylamide, diallyl ether, polyallyl polyglyceryl ethers or allyl ethers of alcohols from the sugar series, such as erythritol, pentaerythritol, arabitol, mannitol, sorbitol or glucose.

Analogous copolymers are described and prepared in French Patent FR-2,416,723 and U.S. Pat. Nos. 2,798,053 and 2,923,692.

This crosslinked copolymer is used in particular in the form of a water-in-oil emulsion comprising 30 weight % of said copolymer, 25 weight % of liquid paraffin, 4 weight % of a mixture of sorbitan stearate and of a hydrophilic ethoxylated derivative and 41 weight % of water. Such an emulsion is marketed under the name "PAS 5161" or alternatively "Bozepol C" by the Company Hoechst.

The acrylamide and 2-acrylamido-2-methylpropanesulfonic acid copolymers used in accordance with the present invention are copolymers crosslinked by a compound possessing olefinic polyunsaturation, such as those mentioned above, and partially or totally neutralized by a neutralizing agent such as sodium hydroxide, potassium hydroxide, ammonia or an amine such as triethanolamine or monoethanolamine.

They can be prepared by copolymerizing acrylamide and sodium 2-acrylamido-2-methylpropanesulfonate by the free radical route by means of initiators of the azobisisobutyronitrile type and by precipitation from an alcohol such as tert-butanol.

Use is more particularly made of copolymers obtained by copolymerization of 70 to 55 mol % of acrylamide and 30 to 45 mol % of sodium2-acrylamido-2-methylpropanesulfonate. The crosslinking agent being used at concentrations of $10^{-4}$ to $4 \times 10^{-4}$ mol per mole of the monomer mixture.

These specific copolymers are preferably incorporated in the compositions of the invention in the form of oil-in-water emulsions containing from 35 to 40 weight % of this copolymer, from 15 to 25 weight % of a mixture of $C_{12}$–$C_{13}$ isoparaffin hydrocarbons, from 3 to 8 weight % of lauryl ether of poly(ethylene glycol) containing 7 mol of ethylene oxide, and water. Such an emulsion is marketed under the name of "Sepigel 305" by the Company Seppic.

The crosslinked acrylamide and methacryloyloxyethyltrimethylammonium chloride copolymer used according to the invention is more particularly a copolymer obtained by copolymerization of acrylamide and dimethylaminoethyl methacrylate quaternized with methyl chloride, followed by crosslinking by a compound possessing olefinic unsaturation, in particular methylenebisacrylamide.

Use is more particularly made of a crosslinked acrylamide-methacryloyloxyethyltrimethylammonium chloride (20/80 by weight) copolymer in the form of a dispersion containing 50 weight % of said copolymer in mineral oil. This dispersion is marketed under the name of "Salcare SC92" by the Company Allied Colloids.

The methacryloyloxyethyltrimethylammonium chloride homopolymer is crosslinked by a compound possessing olefinic unsaturation, such as those defined above, in particular methylenebisacrylamide. Use is more particularly made of the homopolymer in the form of a dispersion containing 50 weight % of said homopolymer in mineral oil. This dispersion is sold under the name "Salcare SC95" by the Company Allied Colloids.

Another subject of the invention relates to cosmetic or dermatological containing hair or skin treatment compositions containing, in a physiologically acceptable aqueous medium, at least the combination of the components (A) and (B) as defined above.

The guar gums or nonionic cellulose gums in accordance with the invention are present in these compositions at active material concentrations of between 0.1 and 10 weight %, and preferably between 0.2 and 5 weight %, with respect to the total weight of the composition.

The crosslinked polymers of the invention are present in the compositions in active material concentrations of between 0.1 and 10 weight % with respect to the total weight of the composition, preferably between 0.5 and 7%.

The cosmetic or dermatological compositions in accordance with the invention are provided in the gel, emulsion or vesicular dispersion form.

When the composition is provided in the gel form, the physiologically acceptable medium is composed of water or of a water and lower alcohol mixture, the alcohol being in particular ethanol.

When the composition is provided in emulsion form, the constituents of the combination in accordance with the invention are present in the aqueous phase. The emulsion is prepared from surface-active agents and oils which are well known in the prior art.

The compositions in accordance with the invention can be provided in the form of a vesicular dispersion of ionic or nonionic amphipilic lipids. They are prepared in particular by swelling the lipids in an aqueous solution in order to form spherules dispersed in the aqueous medium, as described in the article by Bangham, Standish & Watkins, J. Mol. Biol., 13, 238 (1965) or in Patent FR-2,315,991 and 2,416,008 of the Applicant Company.

The various types of preparation processes are described in "Les liposomes en biologie cellulaire et pharmacologie [Liposomes in Cell Biology and Pharmacology]", published by INSERM/John Libbery Eurotext, 1987, pages 6 to 18.

The constituents of the combination in accordance with the invention are in the aqueous phase of the dispersion.

The compositions according to the invention can additionally contain adjuvants commonly used in cosmetics or dermatology, such as fragrances, dyes, preservatives, sequestering agents, vegetable, animal or synthetic oils, sunscreens, agents for combating free radicals, surface-active agents, anionic, nonionic, cationic or amphoteric natural or synthetic polymers, proteins, which may or may not be quaternized, silicones, conditioning agents, anti-grease agents, moisturizing agents or propellants.

The cosmetic or dermatological compositions intended for hair treatment and care can be used in the form of a hair gel or cream for combating hair loss or dandruff or of a styling gel.

The compositions according to the invention intended for skin treatment and care can be packaged in the form of a gel or cream for skin care, of a shaving product or of a sun cream or gel.

The compositions according to the invention can be applied topically in dermatology. They contain, in an effective amount, a dermatologically active substance such as vitamin A, carotenoids, natural pigments, retinoids, depigmenting agents, antiseborrheic, antiacne, anti-inflammatory or antidandruff agents or agents for combating hair loss.

A process for the cosmetic treatment of hair according to the invention consists in applying the compositions as defined above to hair, according to the use envisaged, and then optionally in rinsing.

A process for the cosmetic treatment of the skin according to the invention consists in applying, to the latter, a composition as defined above and optionally in rinsing.

The following examples are intended to illustrate the invention without having any limiting nature.

PREPARATION EXAMPLES

Example 1

A styling gel is prepared with the following composition:

| | |
|---|---|
| Crosslinked acrylamide-sodium 2-acrylamido-2-methylpropane-sulfonate copolymer emulsion, sold containing approximately 40% of copolymer under the name "Sepigel 305" by the Company Seppic | 1 g of copolymer |
| Hydroxypropylcellulose sold under the name "Klucel H" by the Company Aqualon | 1 g |
| Ethanol | 8.5 g |
| Fragrance, dye, preservative q.s. | |
| Demineralized water q.s. for | 100 g |

Example 2

A styling gel is prepared with the following composition:

| | |
|---|---|
| Crosslinked acrylamide-ammonium acrylate copolymer water-in-oil emulsion, sold containing 30% of copolymer under the name "PAS 5161" by the Company Hoechst | 3 g of copolymer |
| Vinyl methyl ether-maleic anhydride monoesterified with butanol copolymer, sold containing 50% of active material (AM) in ethanol under the name "Gantrez ES 425" by the Company ISP (100% neutralized with 2-amino-2-methyl-1-propanol) | 1 g AM |
| Hydroxypropylmethylcellulose sold under the name "Methocel F 4M Standard" by the Company Dow Chemical | 2 g |
| Fragrance, dye, preservative q.s. | |
| Demineralized water q.s. for | 100 g |

Example 3

A styling gel is prepared with the following composition:

| | |
|---|---|
| Dispersion in mineral oil of crosslinked acrylamide-methacryloyloxyethyltrimethylammonium chloride copolymer, sold containing 50% of copolymer under the name "Salcare SC 92" by the Company Allied Colloids | 2.5 g of copolymer |
| Hydroxypropylated guar gum, sold under the name "Jaguar HP 8" by the Company Meyhall | 1.5 g |
| Vinylpyrrolidone-methacrylamidopropyltrimethylammonium chloride (85/15) copolymer, sold as an aqueous solution containing 20% of active material under the name "Gafquat HS 100" by the Company ISP | 0.5 g AM |
| Wheat protein hydrolysate, sold as an aqueous solution containing 20% of active material under the name "Hydrotriticum 2000" by the Company Croda | 0.2 g AM |
| Oxyethylenated polydimethylsiloxane, sold under the name "Silwet L 7602" by the Company Union Carbide | 0.2 g |
| Fragrance, dye, preservative q.s. | |
| Demineralized water q.s. for | 100 g |

Example 4

A gel for combating hair loss is prepared with the following composition:

| | |
|---|---|
| Crosslinked acrylamide-sodium 2-acrylamido-2-methylpropane-sulfonate copolymer emulsion, sold containing approximately 40% of copolymer under the name "Sepigel 305" by the Company Seppic | 3 g of copolymer |
| Methylcellulose sold under the name "Methyl Cellulose 200" by the Company Laserson Sabetay | 1 g |
| Methyl nicotinate | 0.1 g |
| Fragrance, dye, preservative q.s. | |
| Demineralized water q.s. for | 100 g |

Example 5

An antidandruff gel is prepared with the following composition:

| | |
|---|---|
| Crosslinked acrylamide-sodium 2-acrylamido-2-methylpropane-sulfonate copolymer emulsion, sold containing approximately 40% of copolymer under the name "Sepigel 305" by the Company Seppic | 10 g of copolymer |
| Hydroxypropylcellulose sold under the name "Klucel H" by the Company Aqualon | 1 g |
| 1-Hydroxy-4-methyl-6-(2,4,4-trimethylpentyl)-2(1H)-pyridinone, monoethanolamine salt, sold under the name "Octopirox" by the Company Hoechst | 0.1 g |
| Ethanol | 35.5 g |
| Fragrance, dye, preservative q.s. | |
| Demineralized water q.s. for | 100 g |

Example 6

A styling gel is prepared with the following composition:

| | |
|---|---|
| Dispersion in mineral oil of crosslinked acrylamide-methacryloyloxyethyltrimethylammonium chloride copolymer, sold containing 50% of copolymer under the name "Salcare SC 92" by the Company Allied Colloids | 1 g of copolymer |
| Hydoxypolymethylcellulose sold under the name "Methocel F4M Standard" by the Company Dow Chemical | 0.3 g |
| Chitosan pyrrolidonecarboxylate, sold under the name "Kytamer PC" by the Company Amerchol | 0.25 g |
| Fragrance, dye, preservative q.s. | |
| Water q.s. for | 100 g |

Example 7

A styling gel is prepared with the following composition:

| | |
|---|---|
| Crosslinked acrylamide-sodium 2-acrylamido-2-methylpropane-sulfonate copolymer emulsion, sold containing approximately 40% of copolymer under the name "Sepigel 305" by the Company Seppic | 1 g of copolymer |
| Hydroxypropylcellulose sold under the name "Klucel H" by the Company Aqualon | 1 g |
| Fragrance, dye, preservative q.s. | |
| Demineralized water q.s. for | 100 g |

Example 8

A styling gel is prepared with the following composition:

| | |
|---|---|
| Crosslinked acrylamide-sodium 2-acrylamido-2-methylpropane-sulfonate copolymer emulsion, sold containing approximately 40% of copolymer under the name "Sepigel 305" by the Company Seppic | 1 g of copolymer |
| Nonionic guar gum, sold under the name "Guargel D/15" by Société francaise des colloïdes | 1 g |
| Fragrance, dye, preservative q.s. | |
| Demineralized water q.s. for | 100 g |

Example 9

A styling gel is prepared with the following composition:

| | |
|---|---|
| Crosslinked acrylamide-ammonium acrylate copolymer water-in-oil emulsion, sold containing 30% | 1 g of copolymer |

-continued

| | |
|---|---|
| of copolymer under the name "PAS 5161" by the Company Hoechst | |
| Hydroxypropylcellulose sold under the name "Klucel H" by the Company Aqualon | 1 g |
| Fragrance, dye, preservative q.s. | |
| Demineralized water q.s. for | 100 g |

Example 10

A styling gel is prepared with the following composition:

| | |
|---|---|
| Dispersion in mineral oil of crosslinked acrylamide-methacryloyloxyethyltrimethylammonium chloride copolymer, sold containing 50% of copolymer under the name "Salcare SC 92" by the Company Allied Colloids | 1 g of copolymer |
| Hydroxypropylcellulose sold under the name "Klucel H" by the Company Aqualon | 1 g |
| Fragrance, dye, preservative q.s. | |
| Demineralized water q.s. for | 100 g |

Example 11

A styling gel is prepared with the following composition:

| | |
|---|---|
| Crosslinked acrylamide-ammonium acrylate copolymer water-in-oil emulsion, sold containing 30% of copolymer under the name "PAS 5161" by the Company Hoechst | 1 g of copolymer |
| Nonionic guar gum, sold under the name "Guargel D/15" by Société francaise des Colloïdes | 1 g |
| Fragrance, dye, preservative q.s. | |
| Demineralized water q.s. for | 100 g |

Example 12

A styling gel is prepared with the following composition:

| | |
|---|---|
| Dispersion in mineral oil of crosslinked acrylamide-methacryloyloxyethyltrimethylammonium chloride copolymer, sold containing 50% of copolymer under the name "Salcare SC 92" by the Company Allied Colloides | 1 g of copolymer |
| Nonionic guar gum, sold under the name "Guargel D/15" by Société francaise des Colloïdes | 1 g |
| Fragrance, dye, preservative q.s. | |
| Demineralized water q.s. for | 100 g |

Example 13

A styling gel is prepared with the following composition:

| | |
|---|---|
| Dispersion in mineral oil of crosslinked methacryloyloxyethyltrimethylammonium chloride homo- | 2 g of polymer |

-continued

| | |
|---|---|
| polymer, sold containing 50% of polymer under the name "Salcare SC 95" by the Company Allied Colloids | |
| Hydroxypropylmethylcellulose sold under the name "Methocel F4M Standard" by the Company Dow Chemical | 1 g |
| Fragrance, dye, preservative q.s. | |
| Water q.s. for | 100 g |

Example 14

A skin care gel is prepared with the following composition:

| | |
|---|---|
| Dispersion in mineral oil of crosslinked acrylamide-methacryloyloxyethyltrimethylammonium chloride copolymer, sold containing 50% of copolymer under the name "Salcare SC 92" by the Company Allied Colloids | 0.5 g of copolymer |
| Hydroxypropylcellulose sold under the name "Klucel H" by the Company Aqualon | 0.25 g |
| Maize oil | 10 g |
| Water q.s. for | 100 g |

Example 15

A sun protection cream is prepared with the following composition:

| | |
|---|---|
| Dispersion in mineral oil of crosslinked acrylamide-methacryloyloxyethyltrimethylammonium chloride copolymer, sold containing 50% of copolymer under the name "Salcare SC 95" by the Company Allied Colloids | 1 g of copolymer |
| Hydroxypropylmethylcellulose sold under the name "Methocel F4M Standard" by the Company Dow Chemical | 0.25 g |
| Rapeseed oil | 10 g |
| 4-tert-Butyl-4'-methoxydibenzoylmethane | 5 g |
| Water q.s. for | 100 g |

I claim:

1. A thickening combination comprising, in an aqueous medium:
    a) a component (A) comprising at least one gum selected from the group consisting of guar gums and nonionic cellulose gums having no hydrophobic group, and having a viscosity, as a 1.5 weight % solution in water, measured with a Drage unit 2 at 25° C., greater than $15 \times 10^{-3}$ Pa.s;
    b) a component (B) comprising at least one cross-linked polymer selected from the group consisting of:
        (i) copolymers of acrylamide and ammonium acrylate;
        (ii) copolymers of acrylamide and partially or totally neutralized 2-acrylamido-2-methylpropanesulfonic acid;
        (iii) copolymers of acrylamide and methacryloyloxyethyltrimethylammonium chloride; and
        (iv) homopolymers of methacryloyloxyethyltrimethylammonium chloride;

the crosslinked polymer/guar gum or cellulose gum ratio, as weight of active material, being between 0.2 and 10.

2. The combination as claimed in claim 1, wherein the guar gum or cellulose gum of the component (A) is selected from the group consisting of hydroxypropylated guar gums, guar gum, methylhydroxypropylcellulose, methylcellulose, hydroxypropylcellulose, hydroxyethylcellulose and methylhydroxyethylcellulose, the viscosities of which, as a 1.5 weight % solution in water, measured with a Drage unit 2 at 25° C., are greater than $15 \times 10^{-3}$ Pa.s.

3. The combination as claimed in claim 1, wherein the polymer of the component (B) is crosslinked by a compound having olefinic polyunsaturation selected from the group consisting of divinylbenzene, tetraallyloxyethane, methylenebisacrylamide, diallyl ether, polyallyl polyglyceryl ethers and allyl ethers of alcohols from the sugar series.

4. The combination as claimed in claim 1, wherein the component (B) is a crosslinked acrylamide-ammonium acrylate (5/95 by weight) copolymer in the form of a water-in-oil emulsion, comprising 30 weight % of said copolymer, 25 weight % of liquid paraffin, 4 weight % of a mixture of sorbitan stearate and of a hydrophilic ethoxylated derivative and 41 weight % of water.

5. The combination as claimed in claim 1, wherein the component (B) is a crosslinked acrylamide-2-acrylamido-2-methylpropanesulfonic acid copolymer partially or totally neutralized by sodium hydroxide, potassium hydroxide, ammonia or an amine, in the form of an oil-in-water emulsion containing 35 to 40 weight % of said copolymer, 15 to 25 weight % of a mixture of $C_{12}$-$C_{13}$ isoparaffin hydrocarbons, from 3 to 8 weight % of lauryl ether of poly(ethylene glycol) containing 7 mol of ethylene oxide, and water.

6. The combination as claimed in claim 1, wherein the component (B) is a crosslinked acrylamide-methacryloyloxyethyltrimethylammonium chloride (20/80 by weight) copolymer in the form of a dispersion containing 50% of said copolymer in mineral oil.

7. The combination as claimed in claim 1, wherein the component (B) is a methacryloyloxyethyltrimethylammonium chloride homopolymer crosslinked by methylenebisacrylamide in the form of a dispersion containing 50% of said homopolymer in mineral oil.

8. A cosmetic or dermatological hair or skin treatment composition, comprising, in a physiologically acceptable aqueous medium, at least the combination of the components (A) and (B) as defined in claim 1.

9. The composition as claimed in claim 8, wherein the guar gum or nonionic cellulose gum of the component (A) is present in active material concentrations of between 0.1 and 10 weight %, and wherein the crosslinked polymer of the component (B) is present in proportions of between 0.1 and 10 weight %, the percentages by weight being defined with respect to the total weight of the composition.

10. The composition as claimed in claim 8 which is in gel or emulsion form or in the form of a vesicular dispersion of ionic or nonionic amphiphilic lipids.

11. The composition as claimed in claim 8, wherein the physiologically acceptable medium is water or an aqueous/alcoholic medium.

12. The composition as claimed in claim 8, which additionally contains an additive commonly used in cosmetics or dermatology, selected from the group consisting of fragrances, dyes, preservatives, sequestering agents, vegetable oils, animal oils, synthetic oils, sunscreens, agents for combating free radicals, surface-active agents, anionic natural polymers, anionic synthetic polymers, nonionic natural polymers, nonionic synthetic polymers, amphoteric natural polymers, amphoteric synthetic polymers, cationic natural polymers, cationic synthetic polymers, quaternized proteins, unquaternized proteins, conditioning agents, propellants, silicones and moisturizing agents.

13. The composition as claimed in claim 8 intended for hair treatment, which is packaged in the form of a hair gel or cream for combating hair loss or dandruff or in the form of a styling gel.

14. The composition as claimed in claim 8 intended for skin treatment, which is packaged in the form of a gel or cream for care, in the form of a shaving product or in the form of a sun cream or gel.

15. A process for the cosmetic treatment of hair, wherein a composition as defined in claim 13 is applied to hair and optionally rinsed.

16. A process for the cosmetic treatment of skin, wherein a composition as defined in claim 14 is applied to the skin.

17. The composition as claimed in claim 8, wherein the guar gum or nonionic cellulose gum of the component (A) is present in active material concentrations of between 0.2 and 5 weight %.

18. The composition as claimed in claim 8, wherein the crosslinked polymer of the component (B) is present in proportions of between 0.5 and 7 weight %.

19. The composition as claimed in claim 8 which additionally contains an effective amount of a dermatologically active substance selected from the group consisting of natural pigments, depigmenting agents, antiseborrheic, antiacne, antiinflammatory and antidandruff agents, and agents for combating hair loss.

* * * * *